US005756681A

United States Patent [19]

Neurath et al.

[11] Patent Number: 5,756,681

[45] Date of Patent: May 26, 1998

[54] METHOD FOR PROVIDING CONTRACEPTION

[75] Inventors: Alexander Robert Neurath, New York, N.Y.; Mary C. Mahony, Norfolk, Va.

[73] Assignees: New York Blood Center, New York, N.Y.; Eastern Virginia Medical School, Norfolk, Va.

[21] Appl. No.: 825,891

[22] Filed: Apr. 2, 1997

[51] Int. Cl.$^{6}$ .......................... C07K 14/00; A61K 38/16

[52] U.S. Cl. .......................... 530/386; 530/380; 530/833; 530/832; 514/2; 514/841; 514/843

[58] Field of Search .................................... 530/380, 386, 530/833, 832; 514/2, 841, 843

[56] References Cited

U.S. PATENT DOCUMENTS 4,511,558 4/1985 Shur et al. .................................. 514/8

5,238,917 8/1993 Fujii et al. .................................. 514/2

OTHER PUBLICATIONS

Neurath et al., 'Bovine (beta)-Lactoglobulin Modified by 3-Hydroxyphathalic Anhydride Blocks the CD4 Cell Receptro for HIV', Nature Medicine, vol. 2, No. 2, pp. 230–234, Feb. 1996.

Phillips, L.G., Whitehead, D.M. and Kinsella, J., *Structure Function Properties of Food Proteins,* Academic Press, San Diego (1994), pp. 75–82.

*Primary Examiner*—Cecilia J. Tsang

*Assistant Examiner*—Anish Gupta

*Attorney, Agent, or Firm*—Frishauf, Holtz, Goodman, Langer & Chick, P. C.

[57] ABSTRACT

A method for preventing pregnancy in a mammal such as a human, by introducing into the reproductive tract of the mammal an effective contraceptive amount of beta-lactoglobulin, either alone or in combination with a pharmaceutically acceptable excipient, carrier or diluent.

15 Claims, 9 Drawing Sheets

METHOD FOR PROVIDING CONTRACEPTION

BACKGROUND OF THE INVENTION

1. Field of the Invention

The present invention concerns a method for decreasing sperm motility. The present invention also relates to a method to impede sperm penetration into the cervical mucus. More particularly, the present invention concerns a contraceptive method by introducing beta-lactoglobulin into the reproductive tract of a female animal, such as a female mammal.

2. Background Information

Adequate sperm motility is known to be an essential prerequisite for successful fertilization. Specifically, sperm must possess vigorous motility to penetrate cervical mucus, migrate through the female reproductive tract to the site of fertilization and penetrate the oocyte's vestments (Yanagimachi, R., (1994), Mammalian Fertilization, IN: Knobil, E. and Neill, J., (eds.), *Physiology of Reproduction*, Raven Press, pp. 189). Compounds that act on spermatozoa to interrupt one or more of these requisite events in the fertilization process provide unique means for contraceptive intervention.

Spermatozoa quickly enter the cervical mucus of women after coitus (Soberero, A. J., MacLeod, (1962), "The Immediate Post-Coital Test", *Fertil Steril*, 13, 184–189) probably by means of contractions during coitus and by their swimming motions. Even though spermatozoa can traverse the reproductive tract and reach the peritoneal cavity within minutes of insemination (Overstreet, J. W., (1993), "Transport of Gametes in the Reproductive Tract of the Female Mammal", IN: Hartmann, J. F. (ed.), *Mechanisms and Control of Animal Fertilization*, Academic Press, New York, pp. 63–75), the majority generally resides in the cervical mucus within the mucosal folds for extended periods of time. (Davajan, V., Nakamura, R. M., Kharmak, "Spermatozoan Transport in Cervical Mucus", *Obstet. Gynecol. Surv.*, 25:1, (1970).

The cervix acts, not only as a reservoir of spermatozoa, but also as a filter such that only a relatively small number of spermatozoa from the ejaculate ever enter the uterus (Hanson, F. W., Overstreet, J. W., (1981), "The Interaction of Human Spermatozoa with Cervical Mucus In Vivo", *Am. J. Obstet. Gynecol.*, 140, 173).

Sperm migration through the female reproductive tract is essential to successful fertilization. The transit of sperm is dependent upon both the functional status of the male gamete, and its interaction with the components of the female tract, which plays an active role in this process (Overstreet, J. W., Katz, D. F., "Interaction Between the Female Reproductive Tract and Spermatozoa", IN: Gagnon C (ed.), *Controls of Sperm Motility: Biological and Clinical Aspects*. CRC Press, Boca Raton, pp. 64–72).

In particular, the cervical mucus can act to restrict sperm movement, particularly of weak and/or abnormal sperm. Therefore contraceptive agents that act on spermatozoa at or just prior to reaching the cervical mucus are ideal for impedance to fertilization, since the effect of these compounds on the sperm would be magnified by the filtering mechanism of the cervical mucus.

A major site of action for potential contraceptives acting on spermatozoa has been to be impede sperm entry into cervical mucus. Numerous spermicidal agents have been formulated into commercially available vaginal contraceptives (Lee, C-H, (1996), Review: In Vitro Spermicidal Tests. Contraception, 54, 131).

Most spermicidal agents formulated into commercially available vaginal contraceptives fall into the category of surface active agents such as the nonionic detergent, nonoxynol-9, and benzylchronium chloride. These spermicidal agents act by damaging sperm membranes and may similarly affect the cells of the female reproductive tract (Chvapil, M., Eskelson, E., Stiffel, V., Oiwen, J. A., Drogemuller, W., (1980), "Studies on Nonoxynol-9 II. Intravaginal Absorption, Distribution, Metlbolism and Excretion in Rats and Rabbits", *Contraception*, 22, 325). Thus some concerns exist regarding the long term safety for women of these compounds (Abrutyn, D., McKenzie, B. E., Nadaskay, N., (1982), "Teratology Study of Intravaginally Administered N-9 Containing Contraceptive Cream in Rats", *Fertil. Steril.*, 37, 113). Therefore, the search for an effective spermicidal agent, which is efficacious as an antifertility agent, but has minimal toxicological effects has been eagerly sought.

U.S. Pat. No. 4,511,558 to Shur describes a contraceptive agent which comprises alpha-lactalbumin. However, with this substance, the primary mechanism of action is suspected to be either at the level of sperm-egg binding, interference with implantation of fertilized eggs or alteration of sperm motility.

U.S. Pat. No. 5,238,917 to Fujii et al. disclose a transvaginal preparation comprising a calcitonin and an absorption promotor comprising a polyoxyethylenealkylphenyl ether and a compound such as an amino acid N-acylated with an aliphatic carboxylic acid.

SUMMARY OF THE INVENTION

It is an object of the present invention to provide a method for decreasing sperm motility.

It is a further object of the present invention to provide a method to impede sperm penetration into cervical mucus.

It is still a further object of the present invention to provide a method for effective contraception, which is non-toxic.

The above objects are satisfied by the present invention.

The present invention concerns a method for preventing pregnancy in a (female) mammal comprising introducing into the reproductive tract of the mammal (more particularly, a human) an effective contraceptive amount of beta-lactoglobulin.

The present invention also relates to a method to reduce sperm motility, i.e., to impede and/or block sperm motility, by introducing into the reproductive tract of a (female) mammal an amount of beta-lactoglobulin to effectively reduce sperm motility.

The present invention is further directed to a method to reduce sperm penetration into the cervical mucus of a mammal by introducing into the reproductive tract of a (female) mammal an amount of beta-lactoglobulin to effectively reduce sperm penetration in the cervical mucus of the mammal.

The beta-lactoglobulin is introduced (administered) to the mammal either alone, or in combination with a pharmaceutically acceptable excipient, carrier or diluent.

BRIEF DESCRIPTION OF THE DRAWINGS

In FIGS. 3A to 3G, the results are expressed as the means ± standard error. Data for FIGS. 3A to 3G were obtained from three donor semen specimens and were analyzed by ANOVA followed by the Bonferroni post test. Bars with different letters in FIGS. 3A to 3G are significantly different, $p<0.01$.

DETAILED DESCRIPTION OF THE INVENTION

Figure 1:
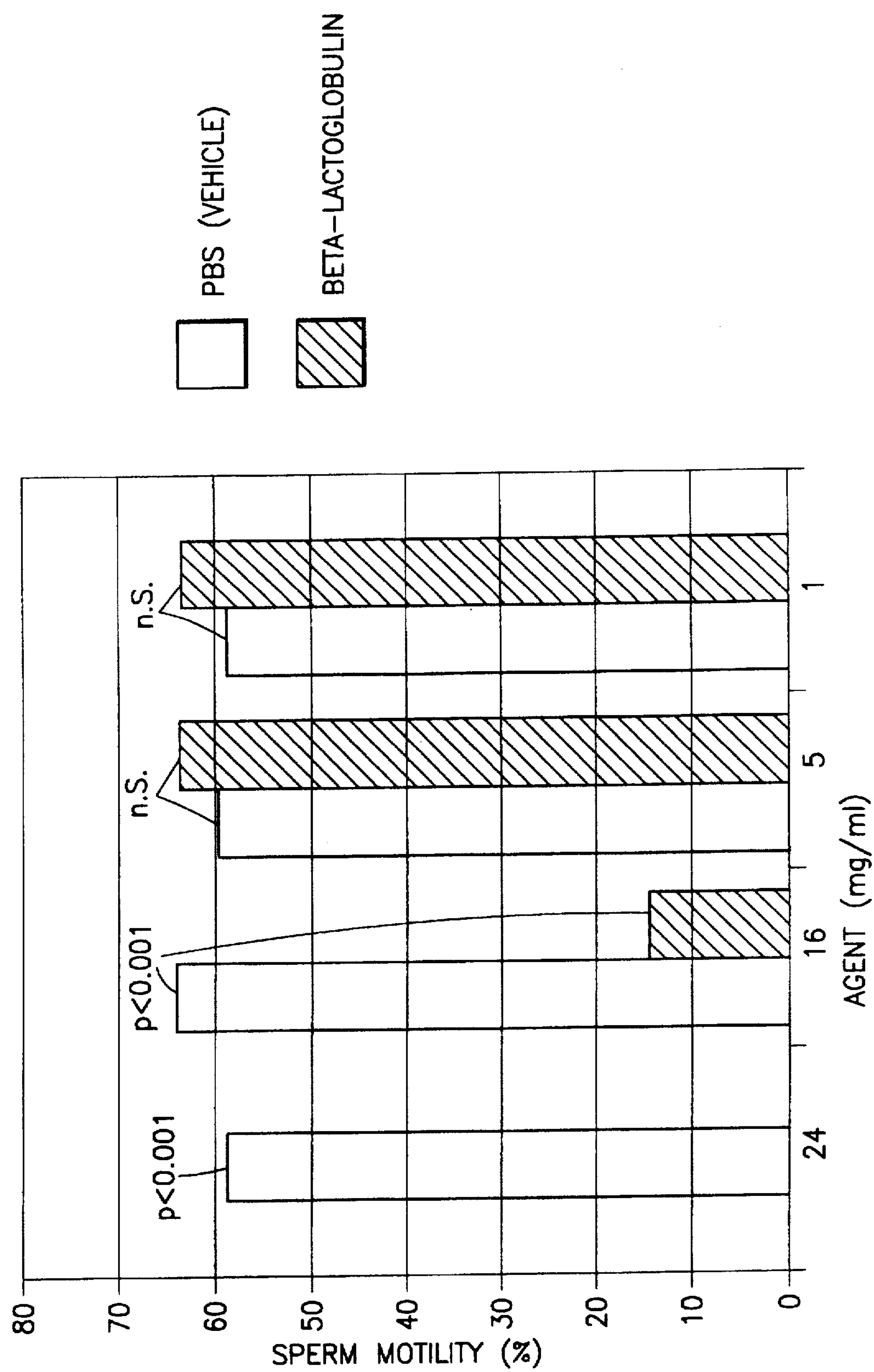
FIG. 1 is a bar graph showing the effect of beta-lactoglobulin on sperm motility. The results in FIG. 1 are expressed as the means ± standard error. The data for FIG. 1 were obtained from three donor semen specimens and were analyzed by student's paired t-test between the treated (beta-lactoglobulin in PBS) group and vehicle (PBS) control group. Bars are presented either with the level of significance above or with n.s. (not significantly different).

The present inventors discovered that beta-lactoglobulin (one of the major components of milk) from non-human sources, for example, cow's milk or goat milk, has potent antifertility actions on human sperm, thus providing an effective and safe contraceptive agent.

Beta-lactoglobulin ("β-LG") is a naturally occurring substance. Beta-lactoglobulin is the most abundant globular protein of milk and the major protein component of whey (2 to 4 g/l) (Phillips, L. G., Whitehead, D. M. and Kinsella, J., *Structure-Function Properties of Food Proteins*, 75–82, Academic Press, San Diego, (1994)). The safety of beta-lactoglobulin is explicit, since beta-lactoglobulin is consumed worldwide as a component of milk products (the worldwide production of whey is approximately 86 billion kg annually) (Morr, C. V. and Ha, E. Y. W., "Whey Protein Concentrates and Isolates: Processing and Functional Properties", *Critical Reviews in Food Science and Nutrition*, 33, 431–476 (1993)).

Beta-lactoglobulin can be readily isolated from the whey fraction of milk by several methods. The stability of beta-lactoglobulin at low pH values (<4.0) is utilized in isolating the protein from whey. As an example, whole milk (containing a mixture of beta-lactoglobulin A and B) is heated to 40° C., followed by the addition of 20 g sodium sulfate per 100 ml milk to precipitate the caseins. The resultant supernatant is cooled down to 25° C. and the pH is adjusted to 2.0 with 11M HCl, causing the other whey proteins to precipitate. Adjustment of the pH to 6.0 with 1M ammonium hydroxide and the addition of 200 g/L ammonium sulfate results in a beta-lactoglobulin-enriched precipitate. This method produces beta-lactoglobulin crystals of high purity. Heating whey solutions to 65° C. in the pH range 4.1 to 4.3 for 30 minutes also permits recovery of the protein from beta-lactoglobulin-enriched supernatants. The isolation of beta-lactoglobulin from precipitates following adjustment of the pH to 4.5 in the presence of 6.7 mM ferric chloride has also been described. Isolated beta-lactoglobulin can be purified by many methods including gel filtration, electrophoresis, and chromatofocusing.

Characterization of beta-lactoglobulin by amino acid composition, sequencing, and isoelectric focusing have demonstrated the existence of genetic polymorphs of the protein. Genetic polymorphism is a characteristic of bovine beta-lactoglobulin and seven different variants, referred to as the A, B, C, D, E, F and G forms have been identified, the most prevalent being the A and B forms. All variants of beta-lactoglobulin possess 162 amino acid residues, however, each variant may differ in one to three amino acid residue positions, which are generally caused by point (single base) mutations in the gene encoding for the protein.

Some chemical and physical properties of the beta-lactoglobulin variants are listed in the following Table 1. The various amino acid residue replacements identified in the variant forms compared to bovine beta-lactoglobulin B are shown in the following Table 2. Although the A and B forms differ at only two positions, the substitution of a Gly residue for an Asp residue at position 4 in the A form is significant because of the increased likelihood of an extra salt bridge forming between the carboxylic group of the Asp residue and any one other basic group in the monomer unit. This particular substitution accounts for the enhanced self-association of beta-lactoglobulin A compared with the B variant.

TABLE 1

Properties of the Genetic Polymorphs of Beta-Lactoglobulin

| Variant | Monomer Mol. Wt. | Isoionic point | Isoelectric point | $Hr_{ave}$* (J/res.) | $A^{1\%}280$ (nm) |
|---|---|---|---|---|---|
| A | 18,363 | 5.35 | 5.15 | 4.53 | 9.6 |
| B | 18,277 | 5.41 | 5.15 | 4.49 | 10.0 |
| C | 18,286 | 5.39 | — | 4.58 | 9.5 |
| D | 18,276 | — | — | 4.58 | — |
| E | 18,205 | — | — | 4.49 | — |
| F | 18,243 | — | — | — | — |
| G | 18,223 | — | — | — | — |

*Hydrophobicity

Beta-lactoglobulins have been isolated and purified from the milks of several different animal species, such as cow, horse, sheep, water buffalo, pig, donkey, deer, kangaroo and dolphin. Beta-lactoglobulin does not appear to be present in the milk of primates nor rodents.

TABLE 2

| | Amino Acid Composition of Bovine Beta-Lactoglobulin B and the Amino Acid Residue Replacements of Genetic Variants | | | | | | |
|---|---|---|---|---|---|---|---|
| | B | A | C | D | E | F | G |
| Asp | 10 | | | Asp —→Tyr | | | |
| Asn | 5 | | | | | | |
| Thr | 8 | | | | | | |
| Ser | 7 | | | | | | |
| Glu | 16 | | Glu→Gln | | | Glu→Gly | Glu→Gly |
| | | Glu→Gly | | | | | |
| Gln | 9 | | Gln→His | | | | |
| Pro | 8 | | | Pro→Ser | | | |
| Gly | 4 | | Gly→Asp | | | | |
| Ala | 15 | | Ala→Val | | | | |
| Cys | 5 | | | | | | |
| Val | 9 | | | | | | |
| Met | 4 | | | | | | |
| Ile | 10 | | | | | Ile→Met | |
| Leu | 22 | | | | | | |
| Tyr | 4 | | | | | | |
| Phe | 4 | | | | | | |
| Trp | 2 | | | | | | |
| Lys | 15 | | | | | | |
| His | 2 | | | | | | |
| Arg | 3 | | | | | | |
| Total = | 162 | | | | | | |

The sequences in the beta-lactoglobulin family have an average of 33 amino acid homology (55 amino acid residues) common to all members, which indicates that these residues are decisive to the structure and conformation of the protein. The quantitative differences among the various beta-lactoglobulin sequences are represented in following Table 3. The highest degree of homology is found in proteins obtained from the milk of ruminants, whereas the degree of sequence homology is much lower among beta-lactoglobulins obtained from monogastric animals, for example, swine and horse. The amino acid sequences from bovine, ovine, porcine, goat and horse beta-lactoglobulins reveal that the highest degree of sequence homology among the proteins occurs in the amino terminal region of each protein molecule and that the positions of the disulfide bonds formed between Cys160–Cys66 and Cys119–Cys106 and the free thiol group on Cys121 are consistent.

The following is an amino acid sequence for bovine beta-lactoglobulin (178 amino acids; molecular weight of 19,883):

MKCLLLALAL TCGAQALIVT QTMKGLDIQK VAGTWYS-
LAM AASDISLLDA QSAPLRVYVE ELKPTPEGDL
EILLQKWENG ECAQKKIIAE KTKIPAVFKI DALNEN-
KVLV LDTDYKKYLL FCMENSAEPE QSLACQCLVR TPE-
VDDEALE KFDKALKALP MHIRLSFNPT QLEEQCHI

The first 16 amino acids in the above sequence correspond to the signal sequence.

Variants for the above sequence are as follows:

E→Q (in variant D).

I→L (in variant W).

Q→H (in variant C, found only in the Jersey breed).

G→D (in variant A).

A→V (in variant A).

F→V

Q→E

Bovine variants and beta-lactoglobulin from other species are expected to be effective in the present invention.

TABLE 3

| | Quantitative Differences in Amino Acid Substitutions of Beta-Lactoglobulins from Various Species | | | | | |
|---|---|---|---|---|---|---|
| | No. of Amino Acid Substitutions | | | | | |
| | Bovine | W. Buffalo | Goat | Ovine | Horse | Swine |
| Bovine | 4 | 8 | 8 | 68 | 62 | |
| W. Buffalo | 2.4 | — | 4 | 4 | 70 | 63 |
| Goat | 4.8 | 2.4 | — | 1 | 70 | 66 |
| Ovine | 4.8 | 2.4 | 0.6 | — | 70 | 66 |
| Horse | 40.9 | 42.1 | 42.1 | 42.2 | — | 80 |
| Swine | 37.3 | 37.9 | 39.7 | 39.7 | 48.1 | — |

Further information concerning the structure and variants of beta-lactoglobulin are found in the following publications:

Variant A

Tissue=Mammary Gland

Alexander L. J., Hayes G., Pearse M. J., Beattie C. W., Stewart A. F., Willis I. M., McKinlay A. G.; *Nucleic Acids Res.*, 17, 6739–6739 (1989).

Variant B

Tissue=Sperm

Hyttinen J. M., Korhonen V. P., Myohanen S., Janne J.; Submitted (February 1995) to EMBL/GENBANK/DDBJ Data Banks.

Sequence of 17–178 Variants A and B

Braunitzer G., Chen R., Schrank B., Stangl A.; *Hoppe-Seyler's Z. Physiol. Chem.*, 354, 867–878 (1973).

Sequence of 28–178 Variant A

Jamieson A. C., Vandeyar M. A., Kang Y. C., Kinsella J. E., Batt C. A.; *Gene*, 61, 85–90 (1987).

Disulfide Bonds

McKenzie H. A., Ralston G. B., Shaw D. C.; *Biochemistry*, 11, 4539–4547 (1972).

Sequence of 59–73 Variant D

Brignon G., Ribadeau-Dumas B.; *Febs Lett.*, 33, 73–76 (1973).

Variant C

Shaw D. C.; Submitted (January 1973) to the PIR Data Bank.

Sequence of 17–178 Variant W

Strain=Murnau-Werdenfelser Godovac-Zimmermann J., Krause I., Buchberger J., Weiss G., Klostermeyer H.; *Biol. Chem. Hoppe-Seyler,* 371, 255–260 (1990).

Revisions to 100, 103, 171 and 172

Preaux G., Braunitzer G., Schrank B., Stangl A.; *Hoppe-Seyler's Z. Physiol. Chem.,* 360, 1595–1604 (1979).

Sequence of 125–138 from Variant A

Willis I. M., Steward A. F., Caputo A., Thompson A. R., McKinlay A. G.; *DNA,* 1, 375–386 (1982).

Secuence of 1–20

Tissue=Pituitary

Silva M. C., Wong D. W. S., Batt C. A.; *Nucleic Acids Res.,* 18, 3051–3051 (1990).

Sequence of 122–178

Ivanov V. N., Judinkova E. S., Gorodetsky S. I.; *Biol. Chem. Hoppe-Seyler,* 369, 425–429 (1988).

X-ray Crystallography

Monaco H. L., Zanotti G.; *Biopolymers,* 32, 457–465 (1992).

Structure by NMR

Molinari H., Ragona L., Varani L., Musco G., Consonni R., Zetta L., Monaco H. L.; *Febs Lett.,* 381, 237–243 (1996).

The potential effects of beta-lactoglobulin on human sperm motility was examined by the inventors with a number of different testing methodologies. Initially, the conventional visual observation was completed on wet preparations of human sperm preincubated with increasing concentrations of the test agent. With this assay, the $ED_{50}$ appeared to be in the range of 16 to 24 mg/ml. Assessment of the proportion of motile sperm in a population can be correlated to fertility (Hanson, F. W., Overstreet, J. W., Katz, D. F., (1982), "A Study of the Relationship of Motile Sperm Numbers in Cervical Mucus 48 Hours After Artificial Insemination with Subsequent Fertility", *Am. J. Obstet. Gynecol.,* 143, 85; and Davis, R. O., Overstreet, J. W., Asch, R. H., Ord, T., Sibler, S. J., (1991), "Movement Characteristics of Human Epididymal Sperm Used for Fertilization of Human Ocytes In Vitro", *Fertil. Steril.,* 56, 1128).

The impact of a contraceptive agent on the sophisticated motion characteristics of sperm velocity and sperm amplitude of lateral head displacement may be important factors with respect of fertilizing capacity in humans (Jeulin, C., Feneux, J. D., Serres, C., Jouannet, P., Guilet-Rosso, F., Belaisch-Allart, J., Frydman, J., Testart, J., (1986), "Sperm Factors Related to Failure of Human IVF", *J. Reprod. Fertil.,* 70, 735; and Chan, S. Y. W., Wang, C., Chan, S. T. H., Ho, P. C., So, W. W. K., Chau, Y. F., Ma, H. K., (1989), "Predictive Value of Sperm Morphology and Movement Characteristics in the Outcome of In Vitro Fertilization of Human Oocytes", *J. In Vitro Fert. Embryo Transfer,* 6, 142).

For movement into the cervix, mucus sperm must be progressively motile sperm. However, this entrance into the cervical mucus is also very dependent upon the swimming velocity and the amplitude of lateral head displacement of the sperm, the latter most probably is related to its need in shearing of the mucus interface to reduce its resistance to penetration (Mortimer, D., Pandya, I. J., Sawers, R. S., (1986), "Relationship Between Human Sperm Motility Characteristics and Sperm Penetration into Human Cervical Mucus In Vitro", *J. Reprod. Fertil.,* 78, 93).

Applicants demonstrate herein that beta-lactoglobulin significantly decreased, in a dose dependent manner, all sperm motion characteristics with the exception of linearity. For the amplitude of lateral head displacement of sperm, negligible lateral movement was observed with an apparent $ED_{50}$ of 8 mg/ml. As observed for infertile patients (Aitken, R. J., Sutton, M., Warner, P. E., Richardson, D. W., (1985), "Relationship Between the Movement Characteristics of Human Spermatozoa and Their Ability to Penetrate Cervical Mucus and Zona-Free Hamster Oocytes", *J. Reprod. Fertil.,* 73, 441), this decrease in lateral head movement of sperm, along with the other motion characteristics of sperm, may be one mechanism for the significant impedance in cervical mucus penetration observed for sperm pretreated with beta-lactoglobulin.

Considering the route of spermicidal agents and the active site, testing of the interaction of the agent with cervical mucus is important for the evaluation of potential contraceptives. The determination of sperm penetrability into cervical mucus proved to be a sensitive indicator of beta-lactoglobulin's effects on human sperm, since a significant decrease was determined at concentrations of 5 mg/ml or greater compared to concentration-matched controls. Another highly sensitive indicator of the effect of beta-lactoglobulin on sperm motility was its effect on the proportion of sperm achieving a hyperactivated state. Sperm hyperactivation is a distinctive, vigorous motility in which sperm exhibit a high amplitude whiplash-like movement. The presence of hyperactivated motility is associated with sperm fertilizing capacity both in vitro and in vivo, (Katz, D. F., Yanigimachi, R., (1980), "Movement Characteristics of Hamster Spermatozoa Within the Oviduct", *Biol. Reprod.,* 22, 759; and Burkman, L. J., Sahaj, D. A., (1984), "Hyperactivated Motility in Human Fertile and Subfertile Sperm Suspensions", *Biol. Reprod.,* 30, 138).

Using beta-lactoglobulin, the proportion of sperm exhibiting hyperactivated motility was reduced, since determination of this motility includes increased curvilinear velocity of sperm and amplitude of lateral head displacement of sperm, both of which were reduced in the presence of beta-lactoglobulin.

Compounds that act on spermatozoa to interrupt one or more of the crucial events leading to fertilization provide unique means for contraceptive intervention. Beta-lactoglobulin, as a naturally occurring substance, with its inhibitory action on sperm motility, is one of these compounds.

The ultimate goal of the method of the present invention is to provide contraceptive intervention so as to prevent contraceptive in an mammal, for example, a human.

As used herein, the terms "contraceptive", "contraceptive agent" and "contraception" are used in their broadest sense to encompass the concept of preventing full-term pregnancy.

As used herein, the terminology of "introduced into the female reproductive tract" means that the beta-lactoglobulin is introduced and dissolved in the vaginal or uterine fluids.

The introduction of beta-lactoglobulin into the female reproductive tract can be achieved by local administration of beta-lactoglobulin, such as application (directly or indirectly) of beta-lactoglobulin to the female genitalia before and/or during sexual contact, such as before sexual intercourse.

The term "locally administration" includes any method of administration such as a topical administration in which the activity of the beta-lactoglobulin is substantially confined to the region of the body to which it is applied, e.g., the vagina.

It is thus preferable to introduce the beta-lactoglobulin by administering a cream, ointment, lotion, jelly, solution, emulsion, spray or foam formulation containing a contraceptive effective amount of the beta-lactoglobulin. Thus beta-lactoglobulin can be introduced, either alone or in combination with a pharmaceutically acceptable carrier, excipient or diluent.

Beta-lactoglobulin can be applied either directly on the female genitalia or can be utilized in conjunction with a contraceptive device by applying the beta-lactoglobulin on a contraceptive device (for example, a male or female condom, a contraceptive diaphragm or a contraceptive sponge, for example, a collagen sponge or a polyurethane foam sponge), prior to sexual intercourse.

Alternatively, the beta-lactoglobulin can be applied on a pessary or tampon for vaginal administration.

The pharmaceutical formulation for topical administration would comprise a pharmaceutically effective contraceptive amount of beta-lactoglobulin and at least one pharmaceutically acceptable topical carrier, excipient or diluent, so as to form an ointment, cream, gel, lotion, paste, jelly, spray or foam.

The amount of the beta-lactoglobulin will vary, not only with the route of administration, and the age and condition of the animal such as a human, to which the beta-lactoglobulin is administered and may ultimately determined by the discretion of a physician. In general, however, a suitable concentration of the beta-lactoglobulin in a topical dosage form is up to 60 milligrams per milliliter, preferably between 10 and 30 milligrams per milliliter.

Concentration levels of the beta-lactoglobulin in the uterine or vaginal fluids can effectively range from about 1% to about 10% (w/v) to produce the contraceptive effect of the present invention. Beta-lactoglobulin should preferably be administered in dosage units varying from about 0.5 mg to about 500 mg.

The present invention involves the use of a pharmaceutical formulation comprising the beta-lactoglobulin, i.e., the active ingredient, by itself or together with one or more pharmaceutically acceptable carriers, excipients or diluents therefor and, optionally, other prophylactic ingredients. The carrier(s), excipient(s) or diluent(s) should be "acceptable" in the sense of being compatible with the other ingredients of the formulation and not deleterious to the recipient therefor.

The pharmaceutical formulations may, where appropriate, be conveniently presented in discrete dosage units and may be prepared by any of the methods well known in the art of pharmacy. All such methods include the step of bringing into association the active ingredient (beta-lactoglobulin) with liquid carriers or finely divided solid carriers or both and then, if necessary, shaping the product into the desired formulation.

Formulations suitable for vaginal administration may be presented as pessaries, tampons, creams, gels, pastes, jelly, foams or sprays or aqueous or oily suspensions, solutions or emulsions (liquid formulations), or films containing in addition to the beta-lactoglobulin, such carriers as are known in the art to be appropriate.

Liquid preparations according to the present invention would include beta-lactoglobulin in a pharmaceutically acceptable liquid carrier or diluent, such as purified water or a physiological saline solution. The liquid preparations may also contain conventional additives, such as suspending agents, emulsifying agents, non-aqueous vehicles (which may include edible oils) or preservatives.

Ointments, pastes, jellies, liquids, foams, gels and creams may, for example, be formulated with an aqueous or oil base with the addition of suitable thickening and/or gelling agents. Lotions may be formulated with an aqueous base or an oil base and will in general also contain one or more emulsifying agents, coloring agents, stabilizing agents, suspending agents, thickening agents or surfactants, such as a nonionic surfactant, for example, a polyoxyethylene higher alcohol ether or polyethylene glycol.

A gel preparation having a high viscosity can be prepared by adding a conventional thickening agent into the above described liquid preparation. Non-limiting examples of thickening agents include cellulose lower alcohol ether, polyvinyl alcohol ("PVA"), polyvinylpyrrolidone ("PVP") and polyoxyethylene oxypropylene glycol block copolymer (such as "PLURONIC").

The pH value of a transvaginal formulation for use in the present invention should preferably have a pH value close to that of the vagina, i.e., 3 to 7, preferably 4 to 6. The pH may be adjusted by an acid or base which is non-toxic and non-irritating to humans, for example, an organic acid such as acetic acid, or citric acid, or a weak base, such as sodium hydrogen carbonate or sodium acetate.

A film preparation for use in the present invention may be prepared by mixing beta-lactoglobulin with the above discussed liquid preparation, with a film base, for example, hydroxypropylmethyl cellulose, chitosan, pullulan, glucomannan or polyacrylate ester.

A tampon-shaped preparation for use in the present invention may be prepared by coating a tampon-shaped core made of silicone resin with a polymer film containing beta-lactoglobulin.

Pharmaceutical formulations suitable for vaginal administration, wherein the carrier is a solid, such as a wax, can be in the form of unit dose suppositories (contraceptive membrane suppositories). Suitable carriers include cocoa butter, agarose, dextran or glycerogelatin, and other materials commonly used in the art, and the suppositories may be conveniently formed by admixture of beta-lactoglobulin with the softened or melted carrier(s) followed by chilling and shaping in molds. Vaginal rings containing inert materials can also be used to introduce beta-lactoglobulin into the female reproductive tract.

Additives that may be used in pharmaceutical compositions containing beta-lactoglobulin may include excipients (such as starch, dextrin, mannitol, cyclodextrin and traganth) binding agents, fillers, colorants (such as beta-carotin) lubricants, isotonic agents (such as sodium chloride or glucose) disintegrants, antioxidants (such as ascorbic acid, erythorbic acid, or a salt or ester thereof) or wetting agents. With respect of additives which are utilized in pharmaceutical compositions, see *Remington's Pharmaceutical Sciences*, 17th, (1985), edited by Gennaro, A. R., Mack Publishing Company, Easton, Pa.

EXAMPLES

The present invention will now be described with reference to the following non-limiting examples.

Example 1

Human Sperm Preparation

Human semen was collected by masturbation from proven fertile men (donors) after 2 to 5 days of sexual abstinence. These men were active participants of the donor program of the Jones Institute for Women's Health, Department of Obstetrics and Gynecology, Eastern Virginia Medical School, 601 Colley Avenue, Norfolk, Va. 23507, and have fathered a child in the last three years.

Following liquefaction at room temperature, the semen samples were subjected to a basic evaluation of sperm characteristics including volume, concentration, percent motility and computer-evaluated sperm motion parameters.

Semen specimens only with volume ≧1.0 ml, percent motility ≧60%, and sperm concentration ≧50 million/ml were evaluated.

Following the initial assessment, treatment of spermatozoa was dependent upon the evaluation to be made. The initial assessment of the in vitro effect of beta-lactoglobulin (Sigma, St. Louis, Mo., three times crystallized) on both sperm motility and sperm penetration into cervical mucus was examined directly on semen specimens. To evaluate the effect of beta-lactoglobulin on the more sophisticated sperm motion characteristics assessed by computer assisted motion analysis, sperm were first processed by standard swimup to remove the seminal plasma (Mahony, M. C., Oehninger, S., Clark, G. F., Acosta, A. A., Hodgen, G. D., (1991), "Fucoidin Inhibits the Zona Pellucida-Induced Acrosome Reaction in Human Spermatozoa", Contraception, 44, 657). For the swimup procedure, each semen specimen was mixed with Ham's F-10 medium (GIBCO, Grand Island, N.Y.) supplemented with 0.5% human serum albumin (HSA) (Irvine Scientific, Irvine, Calif.) and washed twice by centrifugation at 270× g for eight minutes. The resulting pellet was overlayered with 200 μl of supplemented medium and incubated for one hour at 37° C. and 5% $CO_2$ in water-saturated air. Following incubation, the motile fraction of sperm in the supernatant was removed for treatment with beta-lactoglobulin or vehicle controls.

Example 2

Sperm Motility Assessment

A visual assessment of the percent motility was made on each treated and control group. Aliquots of semen were incubated for 20 minutes with increasing concentrations (0, 1, 5, 16, 24 mg/ml) of beta-lactoglobulin or phosphate buffered saline (vehicle control). After incubation, 20 μl of control or treated sperm was placed on a microscope slide and mounted with a coverslip. At least 100 sperm were counted in each wet preparation. Sperm were classified as nonmotile or with forward progressive motility.

Example 3

Computer-Assisted Sperm Motion Assessment

Sperm motion was also evaluated with the computer assisted motion analyzer, HTM-IVOS (Hamilton-Thorn Research, Danvers, Mass.) as described by Mahony, M. C., Alexander, N. J., Swanson, R. J., (1988), "Evaluation of Semen Parameters by Means of Automated Sperm Motion Analyzers", *Fertil. Steril.*, 49, 876; and Mahony, M. C. et al. (1991), *Contraception*, 44, 667).

The concentration of motile sperm processed by the swimup procedure was adjusted to 15 to 25 million sperm/ml. Sperm were incubated with increasing doses of bovine beta-lactoglobulin (Sigma, St. Louis, Mo.) or phosphate buffered saline (2.7 mmKCl, 1.1 mM $KH_2PO_4$, 0.5 mM MgCl, 138 mM NaCl, 8.1 mM $Na_2HPO_4$) (vehicle control) for 20 minutes at 37° C. and 5% $CO_2$ in water-saturated air. Controls also included sperm incubated only in Ham's F-10 medium (GIBCO, Grand Island, N.Y.) supplemented with HSA.

For assessment, 3 μl of each treated or control sperm sample was loaded into a Microcell loading chamber (20 μm depth) (Fertility Technologies, Natick, Mass.). Each chamber was transferred to the HTM-IVOS where it was maintained at 37° C. for 1 minute prior to the start of data acquisition.

Data collection was completed on randomly selected fields along the length of the Microcell chamber until at least 100 motile sperm were analyzed. The pertinent settings used during the computerized assessment were as follows: (i) analysis during 0.67 seconds; 30 frames); (ii) frame rate: 60 Hz; (iii) minimum contrast: 85; (iv) minimum cell size: 4 pixels; (v) low VAP cutoff: 5.0 μm/seconds; (vi) head size, nonmotile: 12 pixels; (vii) head intensity, nonmotile: 130; and (viii) slow cells were accepted as motile.

At the onset of each experiment, it was verified whether the settings permitted accurate differentiation of motile sperm versus nonmotile sperm or debris by utilizing the "playback option". During "playback", the motions of sperm in the previous field were replayed: a green dot was located over the head of all motile sperm for each frame and a red dot was positioned over the head of nonmotile spermatozoa.

Using the computerized motion analysis, the following motion characteristics of sperm were compared among the control and treated groups: % motility, path velocity (VAP, the average velocity of the smoothed cell path), straightline velocity (VSL, the velocity based on the first and last head positions only), curvilinear velocity or track speed (VCL, the velocity derived from all 30 head positions), maximal amplitude of lateral head displacement (ALH, a measure of the side-to-side movement of the head), and linearity (LIN) (VSL/VCL, a measure of the straightness of trajectory). To differentiate sperm exhibiting hyperactivated motility from those that were not hyperactivated, the following settings were utilized in the SORT program for HTMIVOS, as described in Burkman, L. J., (1991), "Discrimination Between Nonhyperactivated and Classical Hyperactivated Motility Pattern in Human Spermatozoa Using Computerized Analysis", *Fertil. Steril.*, 55, 363; VCL: 100 to 500 μm/seconds; VSL: 20 to 500 μm/seconds; ALH: 7.5 to 50 μm; and LIN: 0 to 65.

Example 4

Sperm-Cervical Mucus Penetration Test

Assessment of the potential effects of beta-lactoglobulin on in vitro sperm-cervical mucus penetration was examined using the commercially available Penetrak kit (Biochem Immunosystems, Allentown, Pa. This in vitro procedure measures the forward progression of sperm within a flat capillary tube filled with bovine cervical mucus and is highly predictive of sperm functional potential (Alexander, N.J., (1981), "Evaluation of Male Infertility with An In Vitro Cervical Mucus Penetration Test",*Fertil. Steril.*, 36, 201). After the initial assessment of the semen to determine that it met minimal standards, an aliquot of semen was mixed with varying concentrations of beta-lactoglobulin or phosphate buffered saline (PBS) as the vehicle control and incubated for 20 minutes at room temperature. After incubation, bovine cervical mucus capillary tubes were placed in the treated and control semen mixtures for 1.5 hours at room temperature. Each capillary tube was removed and the capillary tube was examined for the penetration of sperm into the mucus. Moving slowly along the capillary tube, the sperm that had traveled the greatest distance (vanguard sperm) was located and the distance (mm) that sperm had traveled was recorded.

Example 5

Statistical Analysis Data were analyzed by analysis of variance (ANOVA) followed by Bonferroni post test or student's paired t-test; P≦0.05 was considered significant. All results are expressed as mean±the standard error.

Results

Sperm Motility

To initially detect the effect of beta-lactoglobulin on sperm motility, undiluted semen specimens were treated with increasing concentrations of either the agent or the vehicle control (phosphate buffered saline) (FIG. 1). Data for each control and treated group was obtained from three donor specimens. A complete loss of motility was observed when sperm were treated with beta-lactoglobulin at a concentration of 24 mg/ml for twenty minutes that was highly significantly different from the vehicle control ($p<0.001$). A significant difference between the treated and control groups was also observed at a concentration of 16 mg/ml ($p<0.001$). At concentrations less than 16 mg/ml, no difference was observed between beta-lactoglobulin and the vehicle control.

Sperm-Cervical Mucus Penetration Test

Figure 2:
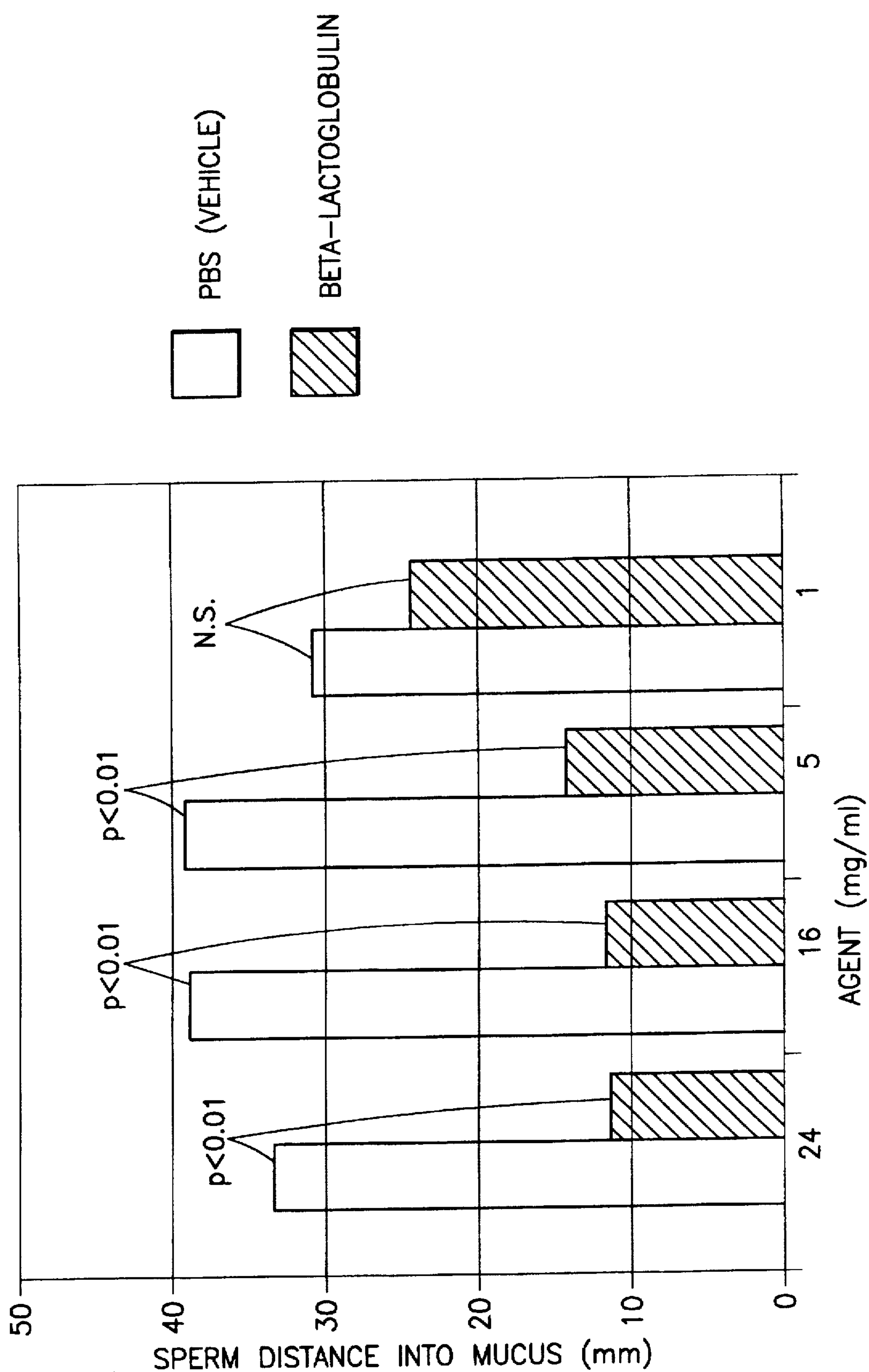
FIG. 2 is a bar graph showing the effect of beta-lactoglobulin on sperm penetration of cervical mucus. The results are expressed as the means ± standard error. Data for FIG. 2 were obtained from three donor semen specimens and were analyzed by student's paired t-test between the treated (beta-lactoglobulin in PBS) group and vehicle (PBS) control group. Bars are presented either with the level of significance above or with n.s. (not significantly different).
Figure 3A:
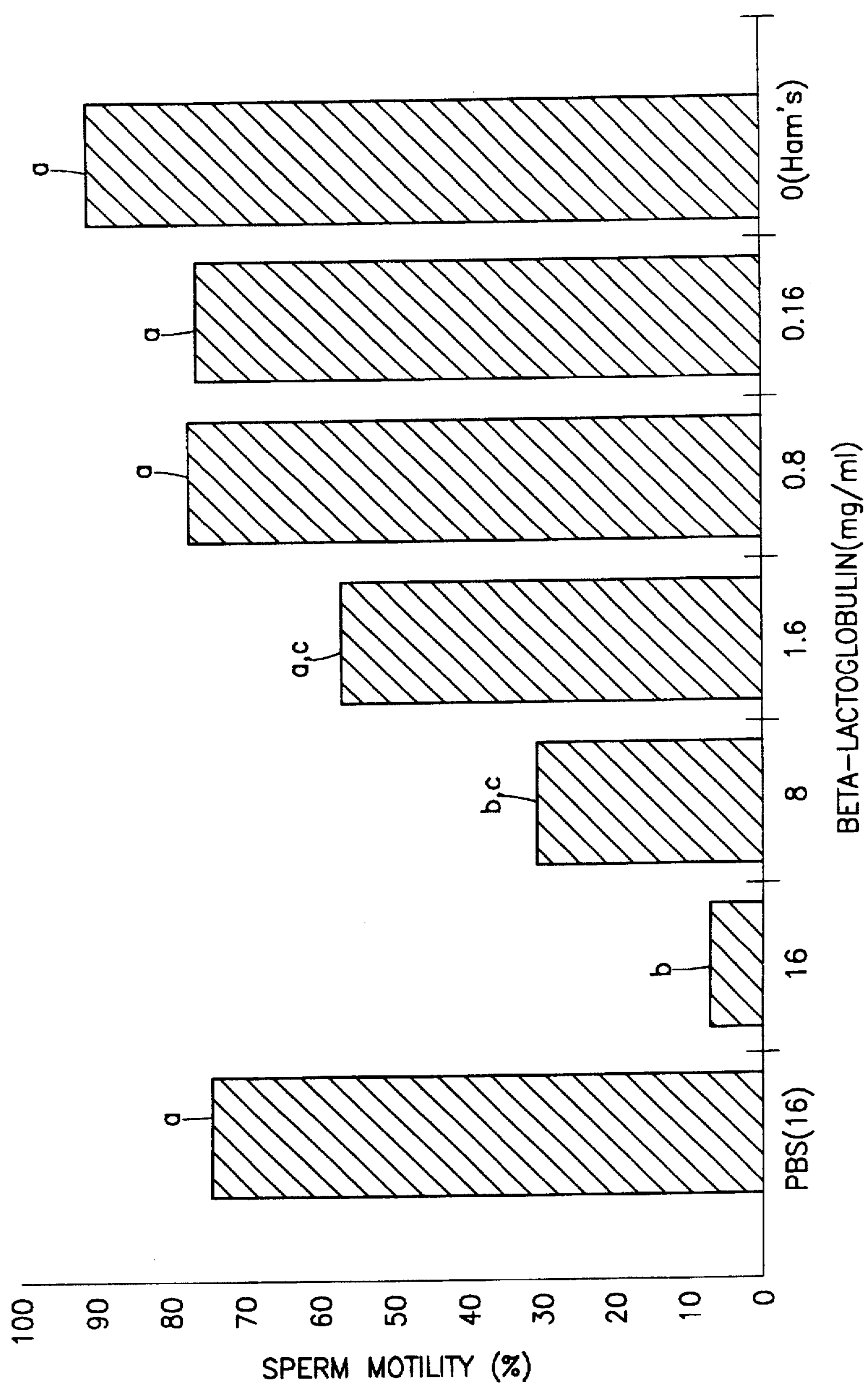
FIG. 3A is a bar graph which shows the effect of beta-lactoglobulin on sperm motility.
Figure 3B:
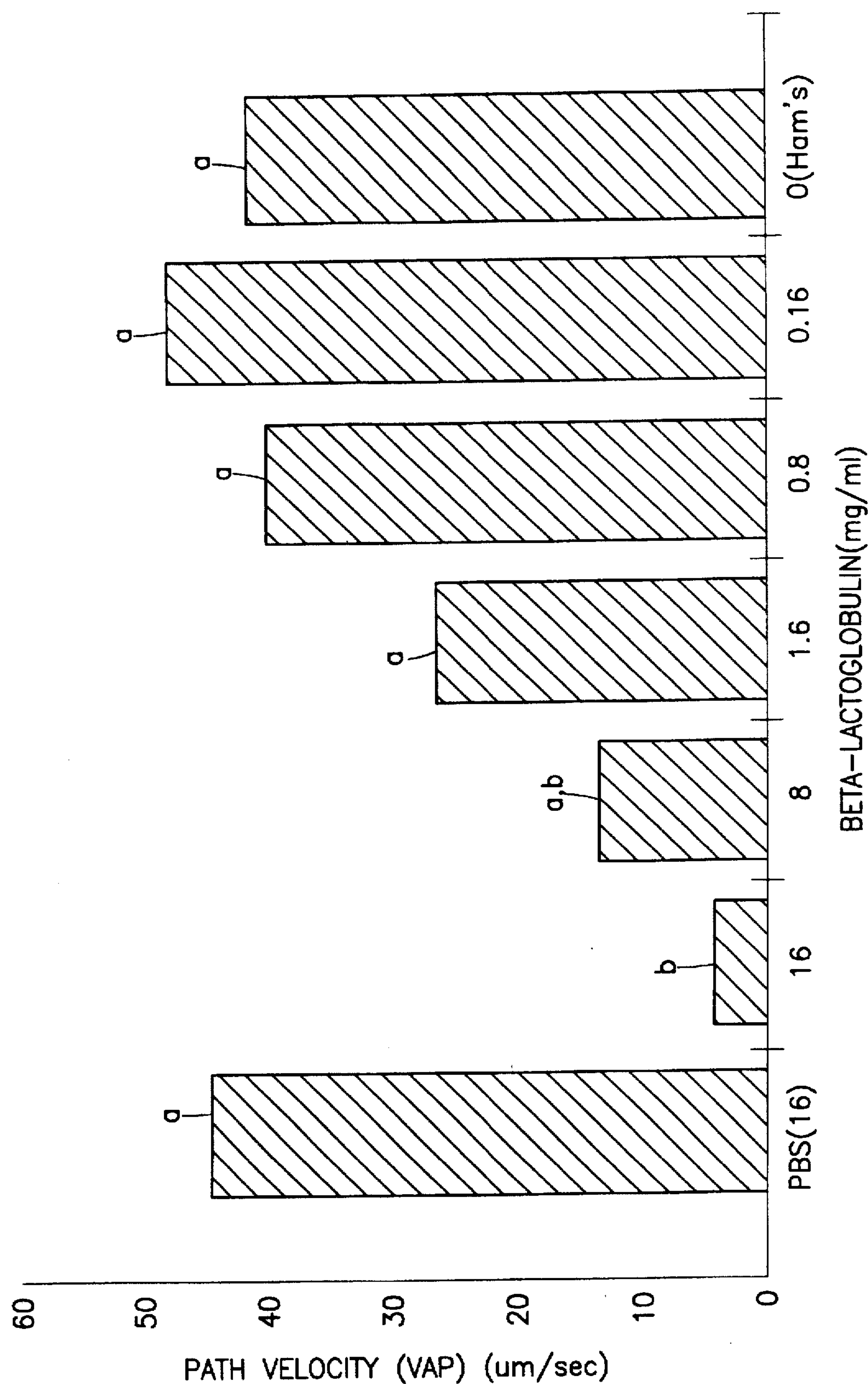
FIG. 3B is a bar graph which shows the effect of beta-lactoglobulin on sperm path velocity ("VAP").
Figure 3C:
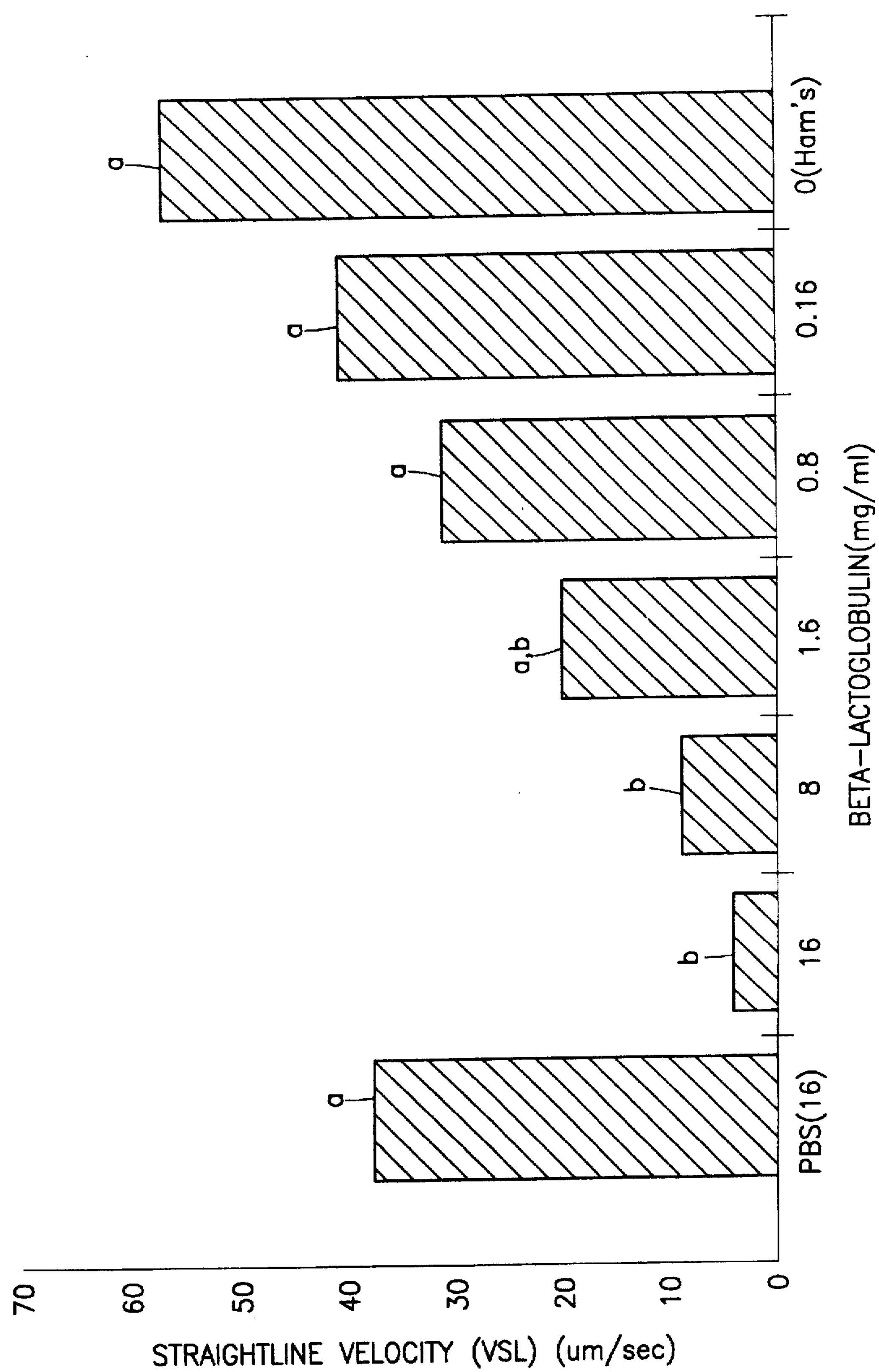
FIG. 3C is a bar graph which shows the effect of beta-lactoglobulin on sperm straightline velocity ("VSL").
Figure 3D:
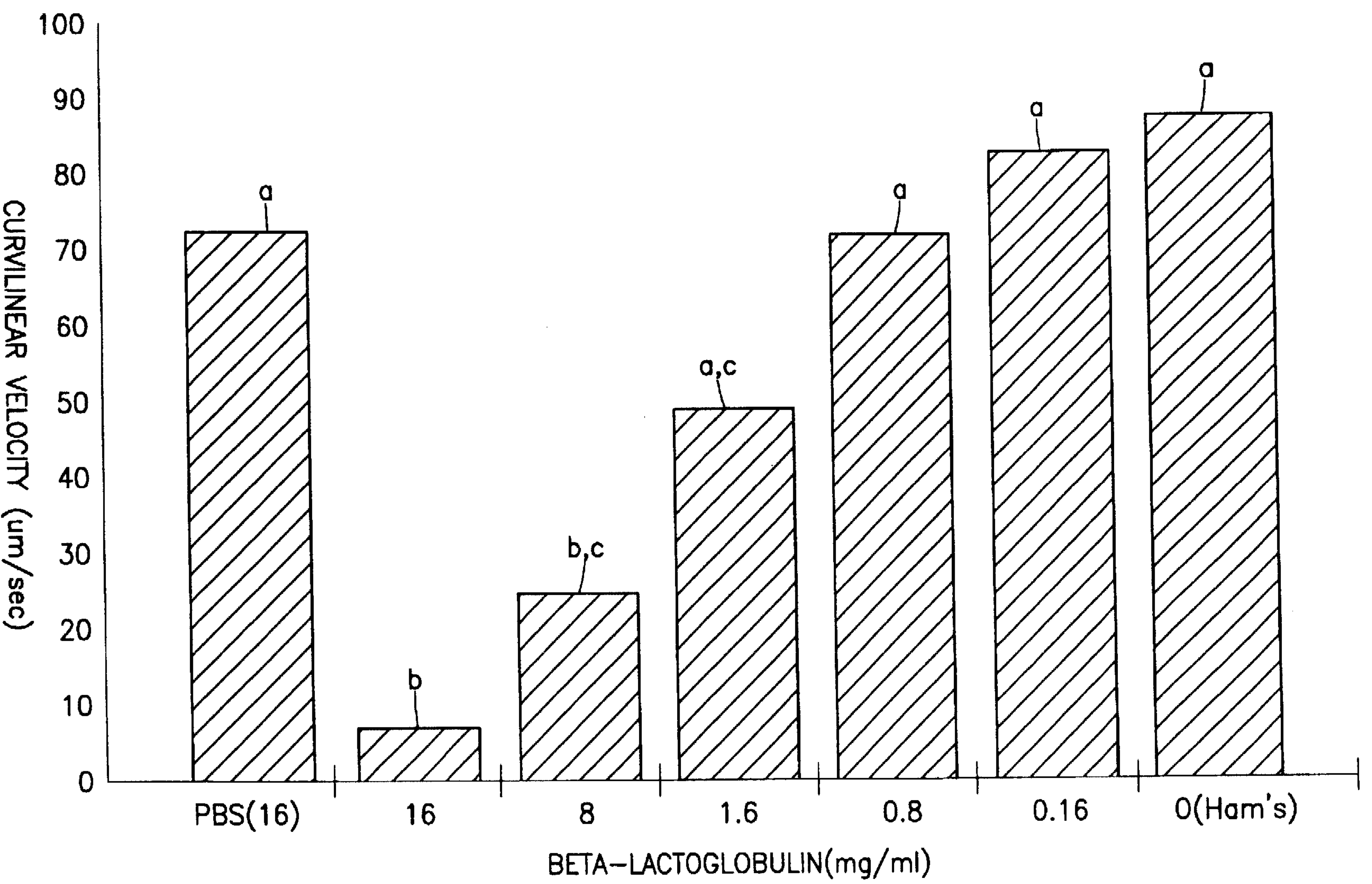
FIG. 3D is a bar graph which shows the effect of beta-lactoglobulin on sperm curvilinear velocity ("VCL").
Figure 3E:
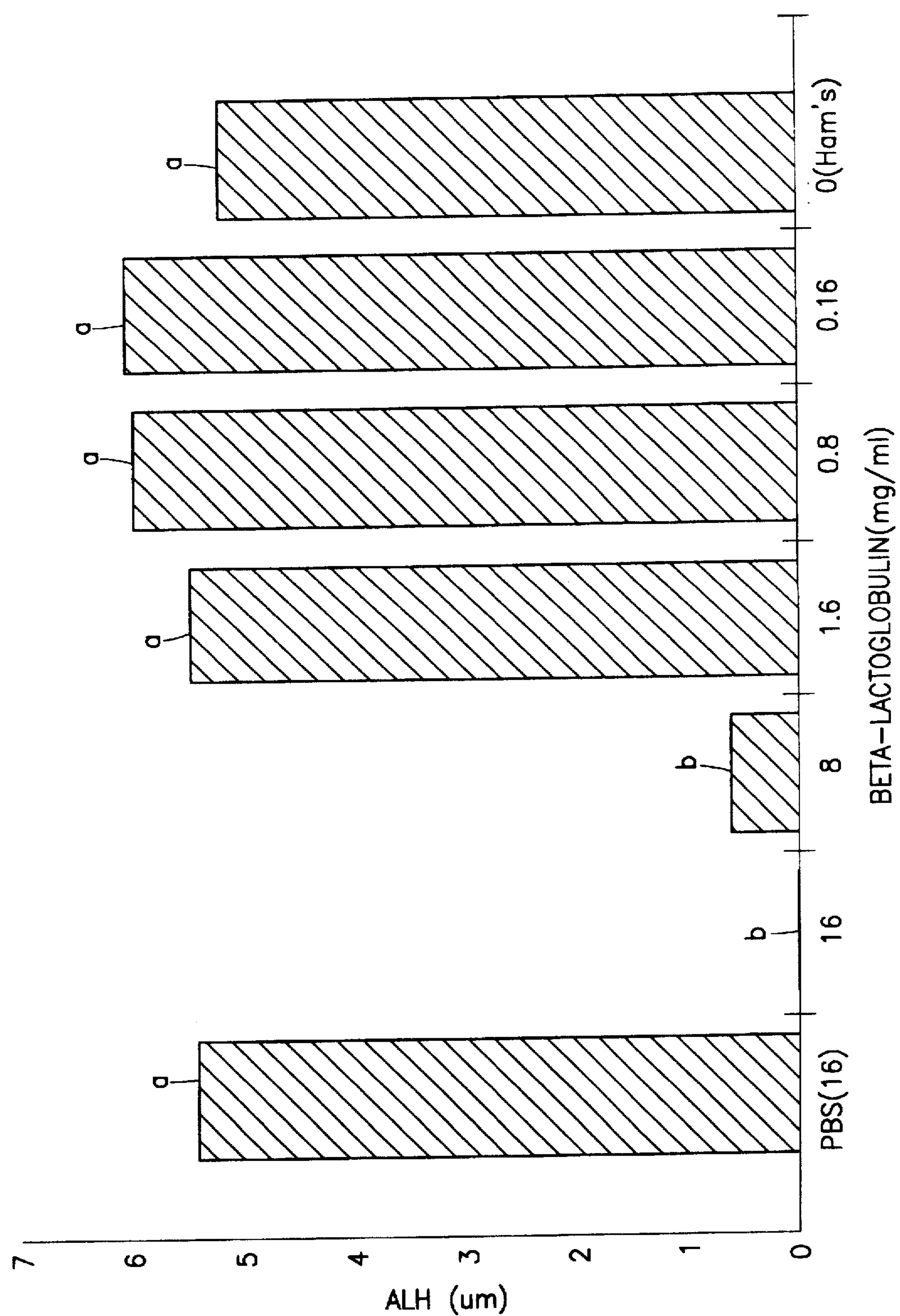
FIG. 3E is a bar graph which shows the effect of beta-lactoglobulin on the amplitude of sperm lateral head displacement ("ALH").
Figure 3F:
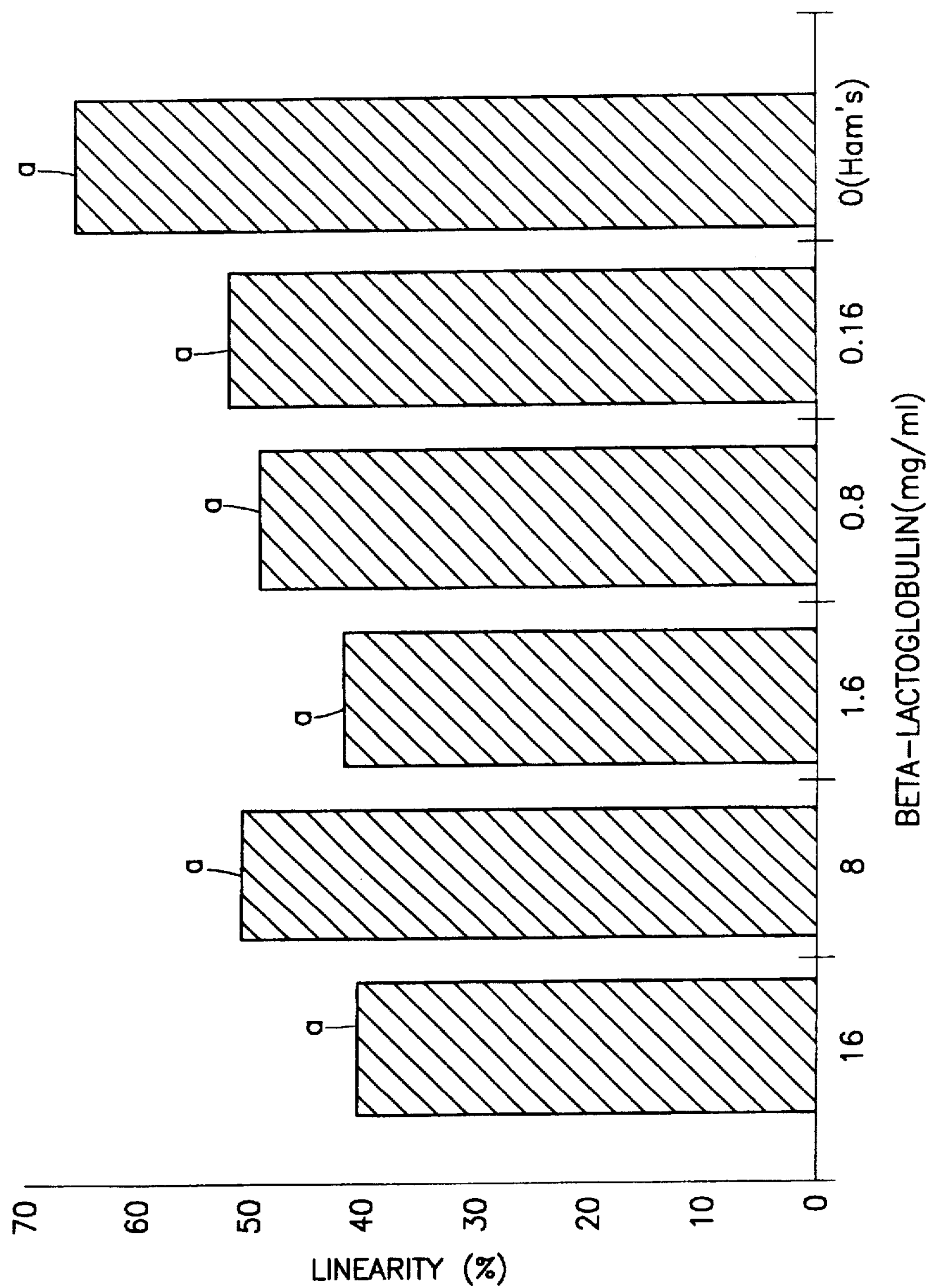
FIG. 3F is a bar graph which shows the effect of beta-lactoglobulin on sperm linearity ("LIN").
Figure 3G:
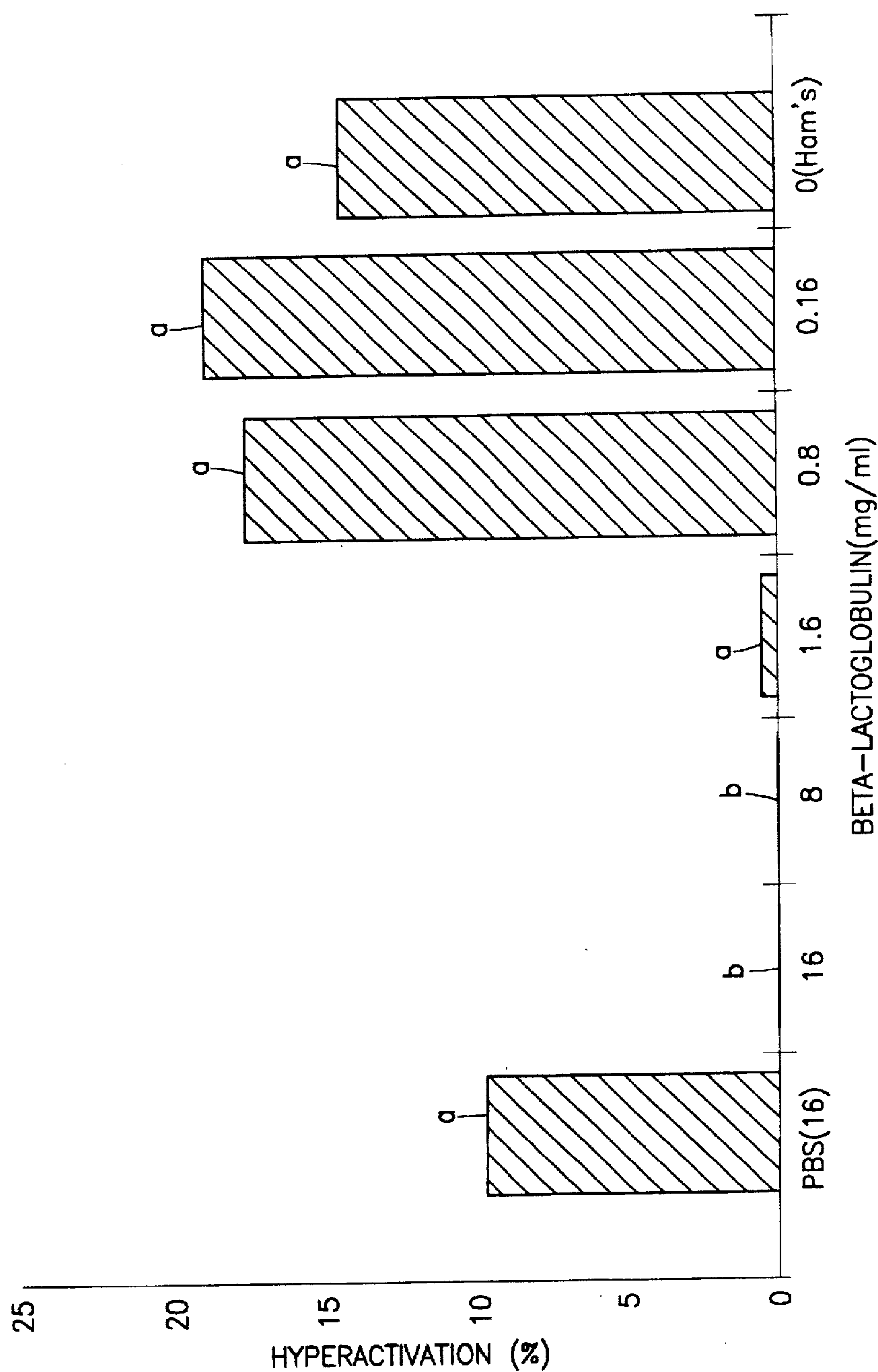
FIG. 3G is a bar graph which shows the effect of beta-lactoglobulin on sperm hyperactivation.

To continue to examine the potential effects of beta-lactoglobulin on sperm motility in semen, semen specimens were again treated with increasing concentrations of the agent or vehicle control. After a preincubation of twenty minutes, their subsequent capacity to penetrate the cervical mucus was determined. The results of the effect of beta-lactoglobulin on sperm-cervical penetration by the vanguard sperm (the sperm traveling the farthest distance into the cervical mucus) are presented in FIG. 2. The distance that the vanguard test sperm traveled along the bovine cervical mucus capillary tube was compared to the distance traveled by the vanguard vehicle (PBS) control sperm. Data for each treatment and control concentration tested was obtained in duplicate from three donor semen specimens. Movement of vehicle control treated sperm into the bovine cervical mucus was consistent with the manufacturer's guidelines for sperm from normal fertile men (≧30 mm). After treatment with concentrations of beta-lactoglobulin from 24 mg/ml to 5 mg/ml, there was a significant difference in the distance traveled by the vanguard sperm in treated compared to vehicle controls ($p<0.01$). At the two higher concentrations, (24 mg/ml and 16 mg/ml), sperm traveled only slightly, if at all, out of the sperm front which routinely makes up the first 5 to 10 mm of the capillary tube. This front is a result of placing the capillary tube in the sperm reservoir which is approximately 5 mm in depth. No significant difference from control was observed for sperm treated with beta-lactoglobulin at a concentration of 1 mg/ml.

Computer-Assisted Sperm Motion Analysis

FIGS. 3A to 3G show the computer-assisted motion analysis that was employed to examine the effect of beta-lactoglobulin on sperm in the absence of seminal plasma. The sperm processing procedure yielded a highly motile sperm fraction. Motion characteristics for the three specimens were as follows: percent motility=91±4%; path velocity (VAP)=40±17 μm/seconds; straightline velocity=56±7 μm/seconds; curvilinear velocity=86±8 μm/seconds; amplitude of lateral head displacement=5.1±0.2 μm; linearity=65%±3; and percent hyperactivation=14%±4. No significant difference was observed in any motion characteristics of sperm pretreated with the vehicle control (PBS) at 16 mg/ml, the highest concentration of test agent. A significant dose dependent inhibition in all motion characteristics was observed for sperm treated with beta-lactoglobulin with the exception of linearity (% motility, VSL, ALH: $p<0.001$; VAP, % hyperactivation: $p<0.02$; VCL: 0.002).

The entire contents of the publications set forth hereinabove are hereby incorporated by reference.

It will be appreciated that the instant specification is set forth by way of illustration and not limitation, and that various modifications and changes may be made without departing from the spirit and scope of the present invention.

What is claimed is:

1. A method for preventing pregnancy in a mammal comprising introducing into the reproductive tract of the mammal an effective contraceptive amount of beta-lactoglobulin, either alone or in combination with a pharmaceutically acceptable excipient, carrier or diluent.

2. The method of claim 2, wherein the mammal is a human.

3. The method of claim 2, wherein the beta-lactoglobulin is introduced by topical administration to the female genitalia prior to sexual intercourse.

4. The method of claim 3, wherein the beta-lactoglobulin is introduced in combination with a pharmaceutically effective excipient, carrier or diluent, to form a cream, lotion, gel, spray, ointment, paste, jelly or foam.

5. The method of claim 2, wherein the beta-lactoglobulin is introduced by applying the beta-lactoglobulin on a male condom, a female condom, a contraceptive diaphragm or a contraceptive sponge, prior to sexual intercourse.

6. The method of claim 5, wherein the beta-lactoglobulin is introduced in combination with a pharmaceutically effective excipient, carrier or diluent, to form a cream, lotion, gel, spray, ointment, paste, jelly or foam.

7. The method of claim 6, wherein the beta-lactoglobulin is introduced by application of the beta-lactoglobulin on a tampon or pessary.

8. The method of claim 2, wherein the beta-lactoglobulin is introduced in the form of a contraceptive membrane suppository.

9. The method of claim 1, wherein the beta-lactoglobulin is introduced in a dosage of 0.5 mg to 500 grams.

10. A method of reducing sperm motility comprising introducing into the reproductive tract of a mammal an amount of beta-lactoglobulin effective to reduce sperm motility.

11. The method of claim 10, wherein the mammal is a human.

12. The method of claim 11, wherein the beta-lactoglobulin is introduced by topical administration to the female genitalia prior to sexual intercourse.

13. A method of reducing sperm penetration into the cervical mucus of a mammal comprising introducing into the reproductive tract of a mammal an amount of beta-lactoglobulin effective to reduce sperm penetration into the cervical mucus of the mammal.

14. The method of claim 13, wherein the mammal is a human.

15. The method of claim 14, wherein the beta-lactoglobulin is introduced by topical administration to the female genitalia prior to sexual intercourse.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 178 amino acids
( B ) TYPE: amino acid
( D ) TOPOLOGY: linear ( i i ) MOLECULE TYPE: protein ( x i ) SEQUENCE DESCRIPTION: SEQ ID NO: 1:

```
Met Lys Cys Leu Leu Leu Ala Leu Ala Leu Thr Cys Gly Ala Gln
-16 -15             -10                 -5

Ala Leu Ile Val Thr Gln Thr Met Lys Gly Leu Asp Ile Gln Lys
-1  1               5                   10

Val Ala Gly Thr Trp Tyr Ser Leu Ala Met Ala Ala Ser Asp Ile
15                  20                  25

Ser Leu Leu Asp Ala Gln Ser Ala Pro Leu Arg Val Tyr Val Glu
30                  35                  40

Glu Leu Lys Pro Thr Pro Glu Gly Asp Leu Glu Ile Leu Leu Gln
45                  50                  55

Lys Trp Glu Asn Gly Glu Cys Ala Gln Lys Lys Ile Ile Ala Glu
60                  65                  70

Lys Thr Lys Ile Pro Ala Val Phe Lys Ile Asp Ala Leu Asn Glu
75                  80                  85
```

-continued

| | | | | | | | | | | | | | | |
|---|---|---|---|---|---|---|---|---|---|---|---|---|---|---|
| Asn | Lys | Val | Leu | Val | Leu | Asp | Thr | Asp | Tyr | Lys | Lys | Tyr | Leu | Leu |
| 90 | | | | | 95 | | | | | 100 | | | | |
| Phe | Cys | Met | Glu | Asn | Ser | Ala | Glu | Pro | Glu | Gln | Ser | Leu | Ala | Cys |
| 105 | | | | | 110 | | | | | 115 | | | | |
| Gln | Cys | Leu | Val | Arg | Thr | Pro | Glu | Val | Asp | Asp | Glu | Ala | Leu | Glu |
| 120 | | | | | 125 | | | | | 130 | | | | |
| Lys | Phe | Asp | Lys | Ala | Leu | Lys | Ala | Leu | Pro | Met | His | Ile | Arg | Leu |
| 135 | | | | | 140 | | | | | 145 | | | | |
| Ser | Phe | Asn | Pro | Thr | Gln | Leu | Glu | Glu | Gln | Cys | His | Ile | | |
| 150 | | | | | 155 | | | | | 160 | | | | |